US009303201B2

(12) United States Patent
Kelland

(10) Patent No.: US 9,303,201 B2
(45) Date of Patent: Apr. 5, 2016

(54) METHOD OF INHIBITING THE FORMATION OF GAS HYDRATES USING AMIDINES AND GUANIDINES

(71) Applicant: ECO INHIBITORS AS, Stavanger (NO)

(72) Inventor: Malcolm Andrew Kelland, Stavanger (NO)

(73) Assignee: ECO INHIBITORS AS, Stavanger (NO)

( * ) Notice: Subject to any disclaimer, the term of this patent is extended or adjusted under 35 U.S.C. 154(b) by 32 days.

(21) Appl. No.: 14/351,131

(22) PCT Filed: Oct. 10, 2012

(86) PCT No.: PCT/EP2012/070073
§ 371 (c)(1),
(2) Date: Apr. 10, 2014

(87) PCT Pub. No.: WO2013/053766
PCT Pub. Date: Apr. 18, 2013

(65) Prior Publication Data
US 2014/0256599 A1 Sep. 11, 2014

(30) Foreign Application Priority Data
Oct. 11, 2011 (GB) .................................. 1117477.8

(51) Int. Cl.
| C09K 8/52 | (2006.01) |
| C09K 8/32 | (2006.01) |
| C09K 8/528 | (2006.01) |
| C10L 3/10 | (2006.01) |
| C07C 277/08 | (2006.01) |

(52) U.S. Cl.
CPC ............. *C09K 8/528* (2013.01); *C07C 277/08* (2013.01); *C09K 8/52* (2013.01); *C10L 3/107* (2013.01); *C09K 2208/22* (2013.01)

(58) Field of Classification Search
CPC ... C09K 8/52; C09K 2208/02; Y10S 507/927
USPC .......................................... 507/90, 129, 236
See application file for complete search history.

(56) References Cited

U.S. PATENT DOCUMENTS

| 3,846,071 A | 11/1974 | Redmore et al. |
| 3,909,200 A | 9/1975 | Redmore |
| 3,943,954 A | 3/1976 | Fluornoy et al. |
| 4,388,213 A | 6/1983 | Oppenlaender et al. |
| 4,457,372 A | 7/1984 | Doster et al. |
| 5,082,968 A | 1/1992 | Brunelle |
| 5,556,938 A | 9/1996 | Freeman et al. |
| 5,874,660 A * | 2/1999 | Colle .................... C08F 226/02 137/13 |
| 6,025,302 A | 2/2000 | Pakulski |
| 7,786,050 B2 | 8/2010 | Parris et al. |
| 7,838,467 B2 | 11/2010 | Jones et al. |
| 2008/0197084 A1* | 8/2008 | Jessop .................. B01D 17/047 210/750 |
| 2009/0286699 A1 | 11/2009 | Saini et al. |

FOREIGN PATENT DOCUMENTS

| FR | 1 430 615 A | 3/1966 |
| GB | 1109431 | 4/1968 |
| RU | 2 108 409 C1 | 4/1998 |
| WO | WO 94/25727 A1 | 11/1994 |
| WO | WO 95/17579 A1 | 6/1995 |
| WO | WO 03/087532 A1 | 10/2003 |
| WO | WO 2005/042675 A2 | 5/2005 |
| WO | WO 2008/023989 A1 | 2/2008 |

OTHER PUBLICATIONS

Kelland, M.A. et al. 2013 "A Breakthrough in Synergists for Kinetic Hydrate Inhibitor Polymers, Hexaalkylguanidinium Salts: Tetrahydrofuran Hydrate Crystal Growth Inhibition and Synergism with Polyvinylcaprolactam" *Energy Fuels* 27 (2): 711-716.

Larionova, I.A. et al. "Guanidine Alkylation" *Russian J Org Chem* 42: 766-767.

Powell, D.A. et al. 2003 "Phase-transfer-catalyzed alkylation of guanidines by alkyl halides under biphasic conditions: a convenient protocol for the synthesis of highly functionalized guanidines" *J Org Chem* 68: 2300-2309.

Khaled, K. F. 2008 "New Synthesized Guanidine Derivative as a Green Corrosion Inhibitor for Mild Steel in Acidic Solutions" *Int J Electrochem Sci* 3: 462-475.

Wang, S. et al. 2009 "Arginine, a key residue for enhancing ability of an antifreeze protein of the beetle Dendroides canadensis" *Biochemistry* 48: 9696-9703.

* cited by examiner

*Primary Examiner* — Aiqun Li

(74) *Attorney, Agent, or Firm* — Knobbe, Martens, Olson & Bear, LLP

(57) ABSTRACT

The present invention relates to methods of inhibiting the formation or agglomeration of gas hydrates using amidines or guanidines. The invention further relates to compositions comprising amidines or guanidines that find use as gas hydrate inhibitors, as well as processes for preparing alkylated amidinium or guanidinium salts.

37 Claims, No Drawings

METHOD OF INHIBITING THE FORMATION OF GAS HYDRATES USING AMIDINES AND GUANIDINES

FIELD OF THE INVENTION

The present invention relates to clathrate hydrate inhibitors and methods of inhibiting the nucleation, formation, agglomeration, and deposition of clathrate hydrates. Methods for preparing hydrate control compounds and hydrate inhibitor compositions are also provided. The invention is especially useful in inhibiting blockages due to clathrate hydrates in pipelines for production and transport of oil and natural gas, in drilling operations, completion, stimulation and fracturing operations, and in injection and re-injection operations.

BACKGROUND OF THE INVENTION

Gas hydrates are clathrates (inclusion compounds) of small molecules in a lattice of water molecules. In the petroleum industry, natural gas and petroleum fluids contain a variety of these small molecules, which can form gas hydrates. They include hydrocarbons such as methane, ethane, propane, isobutane as well as nitrogen, carbon dioxide and hydrogen sulphide. Larger hydrocarbons such as n-butane, neopentane, ethylene, cyclopentane, cyclohexane and benzene are also hydrate-forming components. When these hydrate-forming components are present with water at elevated pressures and reduced temperatures, the mixture tends to form gas hydrate crystals. For example, ethane at a pressure of 1 MPa forms hydrates only below 4° C., whereas at 3 MPa gas hydrates can only form below 14° C. These temperatures and pressures suited to hydrate formation are typical operating environments where petroleum fluids are produced and transported and in drilling, completion or fracturing operations in the oil and gas industry.

If gas hydrates are allowed to form inside a pipe containing natural gas and/or other petroleum fluids, they can eventually block the pipe. The hydrate blockage can lead to a shutdown in production and significant financial loss. The oil and gas industry therefore uses various means to prevent the formation of hydrate blockages in pipelines. These include heating the pipe, reducing the pressure, removing the water and adding thermodynamic inhibitors (antifreezes) such as methanol and ethylene glycols, which act as melting point depressants. Each of these methods is costly to implement and maintain. The most common method used today is the addition of antifreezes. However, these antifreezes have to be added at high concentrations, typically 10-60% by weight of the water present, in order to be effective. Recovery of the antifreeze is also often required and is a costly procedure.

An alternative to the above methods is to control the gas hydrate formation process using nucleation and crystal growth inhibitors. These types of chemicals are widely known and used in other industrial processes. The advantage of using these chemicals to control gas hydrate formation is that they can be used at concentrations of 0.01 to 3%, i.e. much lower than concentrations typically used for antifreezes. Thus, these chemicals are often called low dosage hydrate inhibitors (LDHIs).

Gas hydrate nucleation inhibitors are called kinetic hydrate inhibitors (KHIs). Examples of KHIs include polyvinylpyrrolidone, copolymers of vinyl pyrrolidinone (e.g. with alpha-olefins, vinyl caprolactam or dimethylaminoethyl methacrylate), polymers containing pyrrolidinocarbonyl aspartate groups, polyesteramides and polyvinyllactams. KHI polymers are often expensive, therefore a lower concentration of KHI polymer (perhaps 40-60% as much) is often used with the addition of a cheaper synergist to improve the performance and lower the overall cost. A commonly used KHI synergist is the quaternary ammonium salt, tetrabutylammonium bromide (TBAB).

Some kinetic hydrate inhibitor polymers cannot be used on some oil/gas fields because they have a cloud point (or lower critical solution temperature) in the produced aqueous fluid below the temperature where the polymer would be injected, e.g. at the wellhead. This would cause the polymer to deposit near the injection point rendering it ineffective for the job for which it was designed. It could also cause a restriction in the conduit near the injection point. It would therefore be advantageous if alternative additives could be found.

Besides KHIs, there is another class of LDHIs called anti-agglomerants (AAs). AAs do not inhibit the formation of gas hydrates to the same level as KHIs, rather their primary activity is in preventing the agglomeration and deposition of hydrate crystals. A hydrocarbon phase provides a transport medium for the hydrates which are referred to as hydrate slurries so that the overall viscosity of the medium is kept low and can be transported along the pipeline. As such, the hydrate crystals formed in the water-droplets are prevented from agglomerating into a larger crystalline mass. Chemicals acting as anti-agglomerate hydrate inhibitors are typically quaternary ammonium or phosphonium salts, such as tributylhexadecylphosphonium bromide and tributylhexadecylammonium bromide.

Unfortunately, such compounds have undesirable levels of toxicity, are poorly biodegradable and don't function well in water with relatively low salt concentrations (such as some areas of the North Sea).

Due to the above-mentioned problems relating to cost, performance and environmental impact, a need exists for alternative compounds for inhibiting and controlling the formation of gas hydrates in connection with hydrocarbon production, storage and transportation including production, drilling, completion, fracturing, stimulation and injection and reinjection operations.

SUMMARY OF THE INVENTION

It is therefore an object of the present invention to find novel and effective compounds which retard the formation of gas hydrates (kinetic inhibitors) or keep the gas hydrate crystals small and pumpable (anti-agglomerants).

It has been surprisingly found that compounds containing (at least partially) alkylated amidine or guanidine groups, including salts, ion pair and cations thereof are effective kinetic hydrate inhibitors, anti-agglomerants and synergists for KHIs.

Amidines are a group of organic compounds sharing a common functional group with the following general structure.

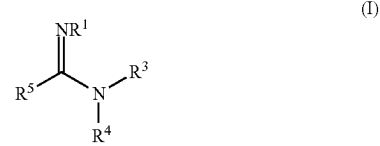

(I)

Guanidines are related compounds in which the central carbon atom (i.e. that attached to a nitrogen atom via a double bond) is attached to two NR$_2$ groups (i.e. such that R$^5$ in the above structure is NR$_2$). Guanidines therefore have the following general formula:

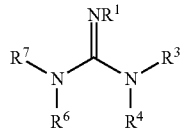

(II)

The respective cationic forms are amidinium ions and guanidinium ions, i.e. of the following general structures respectively:

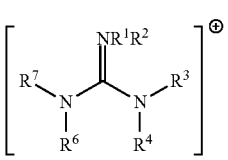

(Ia)

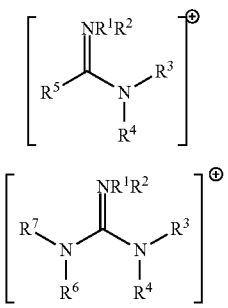

(IIa)

An alternative depiction of the cationic moieties of Formulae (Ia) and (IIa), showing delocalisation of the cationic charge over 2 or 3 nitrogen atoms, is given below:

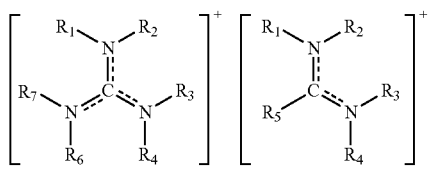

It has been surprisingly found that compounds containing one or more structural units selected from the above, (i.e. those of Formulae (I), (Ia), (II) and (IIa)), can inhibit the formation of hydrates and/or prevent agglomeration of hydrate crystals. Thus, the present invention provides alternative compounds for inhibiting and controlling the formation of gas hydrates in connection with hydrocarbon production, storage and transportation including production, drilling, completion, fracturing, stimulation and injection and reinjection operations. The compounds can act as synergists for new or existing KHI polymers, as anti-agglomerants and as kinetic hydrate inhibitors themselves.

This, viewed from a first aspect, the present invention provides a method of inhibiting the formation or agglomeration of gas hydrates in a system, said method comprising adding to the system a compound or mixture of compounds comprising one or more groups selected from amidine groups, guanidine groups, amidinium ions and guanidinium ions and derivatives thereof, e.g. a compound or mixture of compounds containing one or more units of formula (I) or formula (Ia):

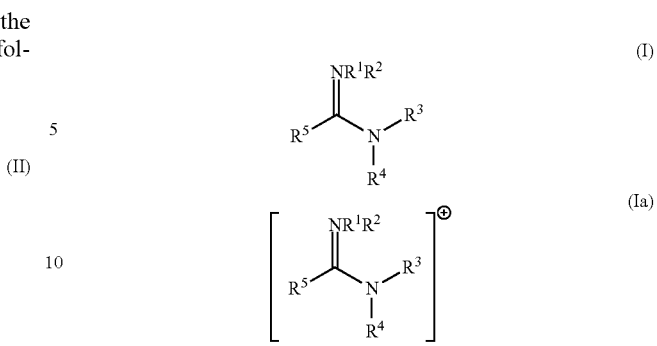

where R$^1$-R$^5$ is an organic moiety and not more than three of R$^1$-R$^5$ are H in any one unit.

Viewed from a further aspect, the invention provides the use of a compound as herein defined for inhibiting the formation or agglomeration of hydrates in a system, preferably a system for hydrocarbon drilling, production, storage and/or transportation, including production, drilling, completion, fracturing, stimulation and injection and re-injection operations.

DETAILED DESCRIPTION OF THE PREFERRED EMBODIMENT

Compositions comprising the compounds described herein form a further embodiment of the invention.

Examples of compounds for the uses, methods and compositions of the invention are amidiniums (salts, cations and ion pairs), guanidiniums (salts, cations and ion pairs), aminoamidines, aminoguanidines, diaminoamidines, diaminoguanidines, diamidines, diguanidines, bis-diamidines, bis-diguanidines, polyamidines and polyguanidines.

Preferably, R$^1$, R$^2$, R$^3$ and R$^4$ are independently H or an organic group comprising 1-20 carbon atoms and optionally one or more heteroatoms, R$^5$ is either H or an organic group comprising 1-20 carbon atoms and optionally one or more heteroatoms or R$^5$ is NR$^6$R$^7$ where R$^6$ and R$^7$ are either H or an organic group comprising 1-20 carbon atoms and optionally one or more heteroatoms, where not more than three of R$^1$-R$^7$ are H in any one unit.

One or more of R$^1$-R$^7$ may be linker groups which attached, for example to a another moiety, e.g. a further unit of structural Formula (I), (Ia), (II) or (IIa) or to a polymer. Especially preferably, one or more of R$^3$-R$^7$ is a divalent moiety such that the amidine, guanidine, amidinium or guanidinium group is part of a larger compound such as a polymer.

Especially preferably the organic group comprising 1-20 carbon atoms and optionally one or more heteroatoms is a C$_{2-20}$ organic group (e.g. an optionally substituted, cyclic, linear or branched saturated or unsaturated hydrocarbon). Especially preferably it is a C$_{2-16}$ alkyl group, especially preferably a C$_{2-6}$ alkyl group, particularly propyl, n-butyl, n-pentyl, iso-pentyl.

Especially preferably all of the R groups in the units of formulae (I), (Ia), (II) and (IIa) are independently selected from butyl, e.g. tert-butyl, n-butyl, sec-butyl or iso-butyl. Especially preferably one or more (e.g. all) of R$^1$-R$^7$ is n-butyl. Particularly preferably R$^5$ is NR$^6$R$^7$.

Especially preferably none of R$^1$-R$^7$ are H.

The most preferred alkyl groups for the R$^1$-R$^7$ moieties are C$_{3-5}$ alkyl groups, especially C$_{4-5}$ alkyl groups. Typically, the compounds containing one or more units of formulae (I), (Ia), (II) and (IIa) contain at least two C$_{2-6}$ alkyl groups. In other words, typically at least two of the $R^1$-$R^7$ groups in the compounds of formulae (I), (Ia), (II) and (IIa) are $C_{2-6}$ alkyl groups.

Preferably, at least two of the $R^1$-$R^7$ groups in the units of formulae (I), (Ia), (II) and (IIa) are $C_{3-5}$ alkyl groups.

Preferably, at least three of the $R^1$-$R^7$ groups in the units of formulae (I), (Ia), (II) and (IIa) are $C_{2-6}$ alkyl groups, more preferably $C_{3-5}$ alkyl groups.

Preferably, at least four of the $R^1$-$R^7$ groups in the units of formulae (I), (Ia), (II) and (IIa) are $C_{2-6}$ alkyl groups, more preferably $C_{3-5}$ alkyl groups.

Preferably, all of the $R^1$-$R^7$ groups in the units of formulae (I), (Ia), (II) and (IIa), excluding the groups which link to an adjacent unit of formulae (I), (Ia), (II) or (IIa) or polymer, are $C_{2-6}$ alkyl groups, more preferably $C_{3-5}$ alkyl groups, except $R^5$ which may also denote $NR^6R^7$.

Thus, in particularly preferred units of formulae (I), (Ia), (II) and (IIa), excluding the groups which link to an adjacent unit of formulae (I), (Ia), (II) or (IIa) or polymer, all of the $R^1$-$R^7$ groups are selected from $C_{2-6}$ alkyl with at least two of the $R^1$-$R^7$ groups denoting $C_{3-5}$ alkyl, preferably $C_{4-5}$ alkyl; except $R^5$ which may also denote $NR^6R^7$.

In the most preferred nits of formulae (I), (Ia), (II) and (IIa), excluding the groups which link to an adjacent unit of formulae (I), (Ia), (II) or (IIa) or polymer, all of the $R^1$-$R^7$ groups are selected from $C_{3-5}$ alkyl with at least two of the $R^1$-$R^7$ groups denoting $C_{4-5}$ alkyl. Typically, the $R^1$-$R^7$ moieties do not combine to form a cyclic amidine. Acyclic alkyl (i.e. linear or branched aliphatic groups) are preferred, preferably not including any heteroatoms.

Thus, as used herein, by the term "alkyl" is meant linear or branched, unsubstituted, acyclic alkyl group containing the recited number of carbon atoms.

In units of formulae (I), (Ia), (II) and (IIa) which contain a $R^1$-$R^7$ group that serves as a linker to an adjacent unit of formula (I), (Ia), (II) and (IIa) or polymer chain, $R^1$-$R^7$ preferably denotes $C_{2-6}$ alkylene, more preferably $C_{3-5}$ alkylene.

The compounds of the invention may be aminoamidines or aminoguanidines, e.g. compounds of the above formulae where one or more of $R^1$-$R^7$ are NR'R" or $N^+$R'R"R'", where R', R" and R'" may be selected from any of the options given for $R^1$-$R^7$, but are preferably lower alkyl groups, e.g. $C_{2-6}$ alkyl, preferably $C_{3-5}$ especially preferably $C_{4-5}$, such as propyl, butyl or pentyl. An example of preferred alkylated aminoguanidines according to the invention in are given below in Schemes 1 and 2.

Scheme 1 - preparation of a butylated aminoguanidine ion

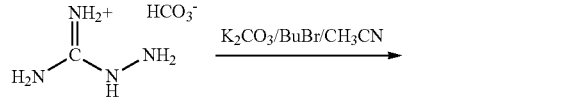

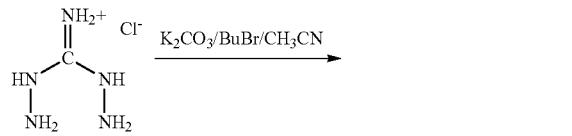

Scheme 2 - preparation of a butylated diaminoguanidine ion

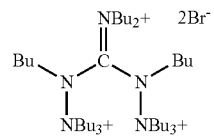

The compounds of the invention may comprise more than one unit of formulae (I) or (Ia), e.g. they may be bis-compounds, di-cations, oligomers or polymers containing two or more, e.g. 2 to 100, preferably 2 to 10, especially 2 to 6 units of the structures herein described. Compounds such as $\{[R_1R_2N=C(NR_3R_4)R_5]\}_2^{2+}X^{2-}$ with anions such as those described below (e.g. sulphate and polyacrylate) are also preferred.

Where the compounds of the invention contain cationic moieties, these may be present in the form of salts or ion pairs with one or more anionic moieties. Amidinium and guanidinium cations, salts and ion pairs are particularly preferred for the uses, methods and compositions of the present invention. The compound of the invention therefore preferably comprises one or more units of formula (Ia), especially one or more units of formula (IIa).

Anions which may be present in the salts and ion pairs of the invention include anionic surfactants such as sodium dodecyl sulphate, alpha-olefin sulphonates, alkoxylated sulphates etc. Other suitable anions are carboxylate, acetate, nitrate, sulphate, phosphate, phosphonate, polyacrylates, polysulphonates and polyphosphonates or halide ions such as chloride, bromide or iodide. Preferred anions are selected from sulphate, polyacrylates, polysulphonates and polyphosphonates or halide ions. In some embodiments, chloride and bromide are suitable anions. However non-halide anions are typically preferred, such as carboxylate, acetate, nitrate, sulphate, phosphate, phosphonate, polyacrylates, polysulphonates and polyphosphonates.

In some embodiments, the compound of the invention may comprise one or more polyamidine or polyguanidine groups, such as diamidine or diguanidine groups, e.g. one or more of $R^3$-$R^7$ may be a moiety of one of the following structures.

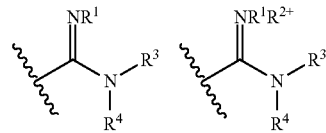

An example of such compounds is shown below in Scheme 3:

Scheme 3 - preparation of a bis-diguanidine

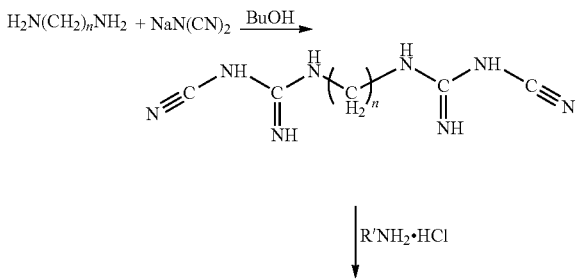

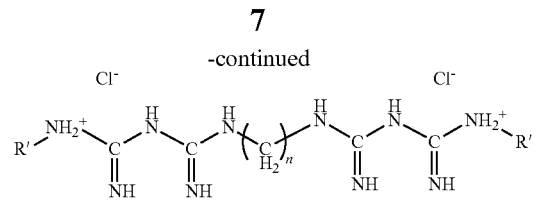

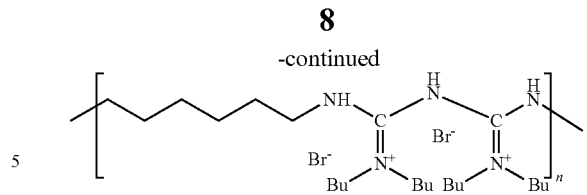

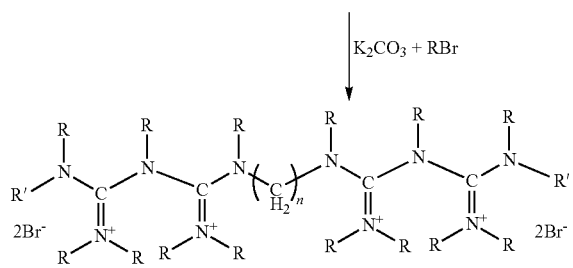

As mentioned above, one or more of $R^1$-$R^7$ may be linker groups which are attached to a polymer. In this way the structural units described above may be connected through one of the R groups to become a pendant group of many oxygen-containing or nitrogen-containing polymers. Such polymers include, but not limited to polyacrylate, polymethacrylate, copolymers of acrylate and methacrylate, polyacrylamide, polymethacrylamide, copolymers of acrylate and methacrylamide, and polymers and copolymers of N-vinylcaprolactam. Such nitrogen containing polymers and copolymers can be obtained by the Michael addition reaction between polyethylenimine and acrylic or methacrylic acids. The copolymers may also include N-vinylcaprolactam, N,N-dimethylacrylamide, N-ethylacrylamide, N-isopropylacrylamide, N-butylacrylamide, or N-tert. butylacrylamide.

As used herein, "poly(meth)acrylate" and "poly(meth)acrylamide" means polymers of acrylarylate (or acrylamide), methacrylate (or methacrylamide), and copolymers of acrylate and methacrlate (or acrylamide and methacrylamide).

The compounds of the methods, uses and compositions of the invention therefore include polymers comprising one or more units of Formula (I) or (Ia). Such polymers preferably have a molecular weight of 200 to 10,000,000 Daltons, preferably 500-5,000,000 Daltons.

Polymers in which the repeat unit consists essentially of units of Formula (I) or (Ia), as well as polymers in which one or more units of Formula (I) or (Ia) are present in the polymer backbone or in one or more side chains are encompassed. Thus one of more of the nitrogen atoms in the amidinium or guanidinium groups can be part of the backbone, or all nitrogen atoms can be in the side chain. Units of formulae (I) or (Ia) may make up the whole or the majority or a minority of the overall polymer and may be positioned randomly or in blocks throughout the overall polymer. The overall polymer may be linear, branched or cross-linked. An example of a preferred polymer for the uses, methods and compositions of the invention is shown below in Scheme 4.

Scheme 4 - preparation of a polyguanidine

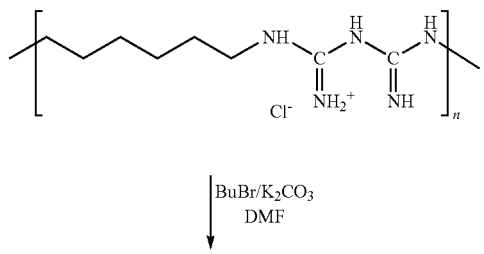

In a further aspect, the compounds for the uses, methods and compositions of the invention may be amphiphiles or surfactants, particularly amphiphiles or surfactants with a molecular weight of less than 1000 Daltons. Where the compound is an amphiphile or surfactant, typically one of $R^1$-$R^7$, preferably one of $R^3$-$R^7$, is or comprises a long chain hydrocarbon group, e.g. a $C_{8-20}$ alkyl group, preferably a $C_{12-18}$ alkyl group such as a hexadecyl group.

In a preferred aspect, the compounds of the invention contain one or more biodegradable linkages such as esters, amides, ethers, or C=C double bonds.

More than one compound as described herein may be added to the system in the method and uses of the invention. For example, mixtures of two or more of the compounds as herein described may be used.

Especially preferred compounds for the methods, uses and compositions of the invention are hexa-n-butylguanidinium bromide, hexa-n-butylguanidinium chloride, hexaethylguanidinium bromide, hexa-n-propylguanidinium bromide, hexa-n-pentylguanidinium chloride, N-hexadecyl-N, N',N',N",N"-penta-n-butylguanidinium chloride and those shown in the schemes above.

The compounds as described herein can be used as kinetic hydrate inhibitors themselves or as synergists (performance enhancing chemicals) for new and existing kinetic hydrate inhibitors, i.e. KHI polymers. In a preferred aspect the method of the invention further comprises adding a kinetic hydrate inhibitor to the system. Use of the compounds herein described as KHI synergists forms a further embodiment of the invention.

The ratio of kinetic hydrate inhibitor to KHI synergist (i.e. a compound of the invention) is preferably from 95:5 to 10:90 by weight.

Examples of KHIs include oligomers, polymers and copolymers of N-vinyllactam, N-vinylcaprolactam, N-vinylpyrrolidone and alkylated vinylpyrrolidones, alkyl- and dialkylacrylamide polymers and copolymers, hyperbranched polymers or dendrimers including polyesteramides, polymers and copolymers of maleic anhydride, which have been reacted with alkylamines to form imide or amide groups, polysaccharides and derivatives of such including sugars and starch, polyoxyalkylenediamines, small alcohols, small glycol ethers or ketones, proteins, peptides polyaminoacids, and amphiphilic molecules with molecular weight of less than 1000 Daltons. Preferably, the kinetic hydrate inhibitor polymer is a polymer, copolymer or graft polymer prepared from or one or more N-vinyl lactams, N-alkylacrylamides, N,N-dialkylacrylamide, N-alkylacrylamides, N,N-dialkylacrylamide, N-vinyl-N-alkyl alkanamides, or a hyperbranched poly(esteramide), or a peptide or protein including polyaspartamides or a polymer or copolymer containing pyroglutamate groups.

In particular, compounds comprising groups of Formula (II) or (IIa) have been found to be very effective as KHI synergists. For example, guanidines according to the present invention have been found to perform better as KHI synergists than tetrabutylammonium bromide (TBAB—a commonly used synergist for KHI polymers). Particularly effective synergists are compounds of Formula (II) or (IIa) wherein one or more $R^{1-7}$ groups contain 2-6 carbon atoms, more preferably 3-5 carbon atoms, for example n-butyl groups. Preferred synergists are salts or ion pairs of the hexa-n-butylguaninidinium ion. Particularly preferred is the use of guanidines as synergists for polyvinyllactams Furthermore, polymers comprising one or more units of formula (I) or formula (Ia) as herein described have been found to be effective as kinetic hydrate inhibitors.

Thus in a further embodiment, the method of the invention is a method is for inhibiting the formation of gas hydrates and said compounds are polymers comprising one or more units of formula (I) or formula (Ia) as herein described.

Thus viewed from a further aspect, the present invention provides the use of a polymer comprising one or more units of formula (I) or formula (Ia) as herein described as a kinetic hydrate inhibitor.

In a further aspect, the method of the present invention is a method for inhibiting agglomeration of gas hydrates. Preferred compounds for this aspect are surfactants comprising one or more units of formula (I) or (Ia) as herein described. Particularly preferred for this aspect of the invention are the cationic forms, (Ia) and (IIa).

Thus viewed from a further aspect, the present invention provides the use of a compound comprising one or more units of formula (I) or (Ia) as herein described as a hydrate anti-agglomerant.

The compositions, methods and uses of the invention are applicable to any system or situation in which gas hydrate formation is desired to be controlled. In particular, they are applicable to systems for hydrocarbon drilling, production, storage and/or transportation, including production, drilling, completion, fracturing, stimulation and injection and re-injection operations. Typically, the "system" referred to herein is a fluid and/or a conduit.

Addition of the compounds to the system may be achieved through any known means and in amounts typical in the art. However, due to the surprising efficacy of the compounds of the invention, lower amounts may be required than of conventional hydrate inhibitor or anti-agglomerant compounds. Typical use concentrations, calculated as 100% of active substance, are 0.005 to 8%, preferably 0.0075 to 5%, more especially 0.01 to 3% especially concentrations of from 0.02 to 1 wt % (100-10,000 ppm) by weight based on the water present in the system.

The present invention is useful for inhibiting hydrate formation or inhibiting agglomeration of hydrates for many hydrocarbons and hydrocarbon mixtures, e.g. those which include methane, ethane, propane, n-butane, isobutane, isopentane and mixtures thereof. Other examples include various natural gas mixtures that are present in many gas and/or oil formations and natural gas liquids (NGL). The hydrates of all of these low-boiling hydrocarbons are also referred to as gas hydrates. The hydrocarbons may also comprise other compounds including, but not limited to $CO_2$, hydrogen sulphide, and other compounds commonly found in gas/oil formations or processing plants, either naturally occurring or used in recovering/processing hydrocarbons from the formation or both, and mixtures thereof.

The methods and uses of the present invention involve contacting a hydrocarbon and water mixture with a compound or composition as described herein. When an effective amount of the compound/composition is used, hydrate blockage is inhibited. The contacting may be achieved by means of standard equipment such as injection pumps or the like, resulting in rapid and uniform distribution of the inhibitor in the aqueous phase which has a tendency to form hydrates.

The contacting can be made in-line or offline or both. When the compounds of the invention are added in a composition, the various components of the composition may be mixed prior to or during contact, or both. If needed or desired, the composition or some of its components may be optionally removed or separated mechanically, chemically, or by other methods known to one skilled in the art, or by a combination of these methods after the hydrate formation conditions are no longer present.

The pressure at which the compounds/compositions are contacted with the hydrocarbon/water mixture is usually at or greater than atmospheric pressure. (i.e. about 101 kPa), preferably greater than about 1 MPa, and more preferably greater than about 5 MPa. The pressure in certain formation or processing plants or units could be much higher, for example greater than about 20 MPa. There is no specific high-pressure limit. The present invention can be used at any pressure that allows formation of hydrocarbon gas hydrates.

Since the inhibitor primarily retards or prevents the formation of gas hydrates, the addition of the inhibitor should ideally take place before gas hydrates are formed, i.e. at above the equilibrium temperature of hydrate formation. The temperature for contacting is usually below, the same as, or not much higher than the ambient or room temperature. Lower temperatures tend to favour hydrate formation, thus requiring the treatment with the compositions/compounds of the present invention. For anti-agglomerant applications, the compounds or compositions may be added before or after hydrate formation, preferably before.

In the methods and uses of the present invention, the compounds and compositions herein described may be added to the system at any stage or location suitable to inhibit formation or agglomeration of hydrates. The conduits into which the compounds/composition of the invention are added are typically hydrocarbon conduits extending for at least part of the length from the site within a hydrocarbon well at which hydrocarbon enters the borehole to the facility remote from the well at which hydrocarbon compositions are processed. Typically, the compounds/compositions are added to a process stream containing hydrocarbons and water by injection via a single port or multiple ports. In one aspect, the compound may be injected into the reservoir matrix surrounding a hydrocarbon production well. In a further aspect, the compound may be injected into a hydrocarbon production well. Preferably, the compound is injected at the well head.

The compounds of the invention may be used alone or together with a further component, such as a hydrate inhibitor, a liquid solvent, a solid carrier and/or an excipient.

A further embodiment of the invention is the provision of hydrate inhibitor or anti-agglomerant compositions. Thus from a further aspect, the present invention provides a hydrate inhibitor or anti-agglomerant composition comprising a compound as herein described and a kinetic hydrate inhibitor, a solvent (e.g. a liquid solvent), a carrier (e.g. a solid carrier) and/or an excipient. In a particularly preferred aspect, the composition of the invention is a hydrate inhibitor composition comprising a kinetic hydrate inhibitor together with a compound as herein described. The compositions may be used in the methods and uses described herein.

Further preferred additives for use together with the compounds of the invention, in the methods, uses and compositions of the invention include polymers, amphiphiles and surfactants. These may be non-ionic or anionic. Examples are alkylpolyglycosides, hydroxylethycellulose, carboxymethylcellulose and other ionic or nonionic surfactant molecules. Especially preferred are anionic surfactants. Other suitable additives are corrosion inhibitors and scale inhibitors.

Suitable solvents, carriers and excipients are known in the art and include oxygenated solvents such as water, alcohols, ether solvents and mixtures thereof. Solvents, carriers or excipients are typically present in the inhibitor compositions in the range from 0 wt % to 95 wt %, e.g. 20 wt % to 95 wt %, preferably 50 wt % to 95 wt % of the total composition.

Preferably, the kinetic hydrate inhibitor polymer is a polymer, copolymer or graft polymer prepared from or one or more N-vinyl lactams, N-alkylacrylamides, N,N-dialkylacrylamide, N-alkylacrylamides, N,N-dialkylacrylamide, N-vinyl-N-alkyl alkanamides, or a hyperbranched poly(esteramide), or a peptide or protein including polyaspartamides or a polymer or copolymer containing pyroglutamate groups.

Especially preferably the KHI is a polyvinyllactam. Particularly preferably the synergist compound is of Formula (II) or (IIa) wherein one or more $R^{1-7}$ groups contain 2-6 carbon atoms, more preferably 3-5 carbon atoms, for example n-butyl groups. Especially preferred compounds for the compositions of the invention are salts or ion pairs of the hexa-n-butylguaninidinium ion.

The ratio of kinetic hydrate inhibitor to compound of the invention is preferably from 95:5 to 10:90 by weight.

Certain of the compounds herein described are novel and thus form a further aspect of the present invention.

The present invention also provides novel methods for preparing compounds used in the methods, uses and compositions herein described. It has previously been reported that alkyl (e.g. hexaalkyl) guanidinium salts are difficult to prepare directly from guanidinium chloride. The applicant has found a novel method for preparing alkyl guanidinium salts directly from guanidinium chloride in a one-pot reaction as exemplified by Scheme 5 below. This reaction has been found to provide higher yields than conventional methods and is simpler and quicker. It is also applicable to amidinium salts.

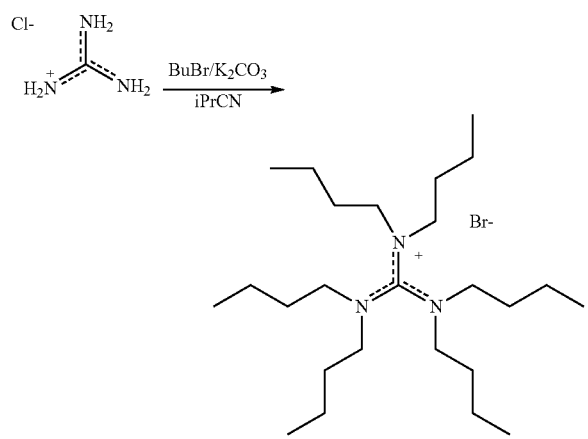

Scheme 5 - one-step alkylation

Thus, from a further aspect, the present invention provides a process for preparing alkylated amidinium or guanidinium salts (especially guanidinium salts), said process comprising the step of refluxing an amidinium or guanidinium salt with a base and an alkylating agent, e.g. an alkyl halide, in a solvent. Preferably the process is one for the formation of a hexaalkylguanidinium salt, e.g. a hexa-n-butyl salt.

Examples of suitable bases are $K_2CO_3$, $NaCO_3$, NaOH, KOH etc. Suitable solvents include acetonitrile, isobutyronitrile etc.

Heating to reflux is required in order to achieve a suitable rate of reaction and the temperature of reflux depends on the solvent used and will be apparent to the skilled person. Reflux duration is typically from 10 to 30 hours, e.g. 15 to 25 hours, e.g. around 20 hours.

The process preferably further comprises removing volatile components from the reaction mixture after refluxing to produce a residue and, optionally, refluxing the residue in an acid such as hydrochloric acid.

Preferred alkylating agents are alkyl halides, alkenes or alcohols. Typical alkenes and alcohols are 1-butene and 2-butanol respectively. A catalyst may be used if necessary. Preferably the alkylating agent is an alkyl halide, such as n-butyl chloride or n-butyl bromide.

Alkylated amidinium and guanidinium salts produced by this process form a further aspect of the invention. They are also applicable to the uses, methods and compositions of the invention.

The compounds described herein, particularly the polymers, may also be used to protect against corrosion, i.e. in some cases it may be unnecessary to use another molecule as a specific corrosion inhibitor if the compounds of this invention can do the job. Alternatively, less corrosion inhibitor may be necessary due to the partial protection provided by the compounds of the invention. The compounds described herein may also have biocidal or scale inhibition properties.

Thus, from a further aspect, the present invention provides the use of a compound as herein defined as a corrosion inhibitor, a biocide or a scale inhibitor.

The invention will now be further described with reference to the following non-limiting examples:

EXAMPLE 1

Synthesis of hexa-n-butylguanidinium bromide via tetra-n-butylurea

A mixture of 5.69 grams (20 mmol) of tetra-n-butylurea, 3.22 grams (21 mmol) of phosphorus oxychloride and 15 ml of acetonitrile was heated at 75° C. in a nitrogen atmosphere for one hour. The mixture was then cooled to 0° C. and 3.36 grams (46 mmol) of n-butylamine was added over 15 minutes with stirring. The mixture was warmed to 60° C. for one hour and again cooled to 0° C., quenched with 5 ml of 25% (by weight) aqueous sodium hydroxide solution and extracted with diethylether. The ether extracts were dried over sodium sulphate, filtered and stripped to give a pale yellow oil of penta-n-butylguanidine.

A mixture of 1.7 grams (5 mmol) of penta-n-butylguanidine (made as described earlier), 0.686 grams (5 mmol) of 1-bromobutane and 10 ml of isobutyronitrile was heated under reflux for 20 hours. Upon vacuum stripping, a pale yellow oil was obtained which crystallized to a pale brown solid upon standing. Upon recrystallization from a mixture of hexane and ethyl acetate, the desired N,N,N',N',N",N"-hexa-n-butylguanidinium bromide was obtained as a white solid.

Other N,N,N',N',N",N"-hexa-alkylguanidinium bromides were made similarly.

EXAMPLE 2

Synthesis of hexa-n-butylguanidinium chloride via guanidinium chloride

Guanidinium chloride (2.0 g, 20.9 mmol), n-butyl chloride (12.78 g, 138.2 mmol), $K_2CO_3$, 19.07 g, 138.2 mmol) and 40 ml acetonitrile were refluxed for 20 hours. The solution was filtered, the acetonitrile removed and the residue refluxed in hydrochloric acid for 20 hrs. The water and excess hydrochloric acid was removed to give an oil which crystallised slowly on standing.

EXAMPLE 3

Synthesis of N-hexadecyl-N,N',N',N",N"-penta-n-butylguanidinium chloride

Hexadecylamine (3 g, 12.4 mmol) was dissolved in 1-butanol (10 ml) and 37% hydrochloric acid (1.23 g, 12.4 mmol) added. The solution was warmed to 95° C. and cyanamide (0.522 g, 12.4 mmol) dissolved in 1-butanol (20 ml) added dropwise with stirring over 10 minutes. The solution was stirred at 95° C. for a further 2 hours. Solvent was removed and the crude product crystallised from ethyl acetate to give a white solid of N-hexadecylguanidinium chloride.

N-Hexadecylguanidinium chloride (4.41 g, 13.8 mmol), n-butyl chloride (6.39 g, 69.1 mmol), $K_2CO_3$, (9.51 g, 69.1 mmol) and 40 m isobutyronitrile were refluxed for 20 hrs. The solution was filtered, the acetonitrile removed and the residue refluxed in isopropyl alcohol and hydrochloric acid for 20 hrs. Solvents were removed to give an oil which is N-hexadecyl-N,N',N',N",N"-penta-n-butylguanidinium chloride.

EXAMPLE 4

Synthesis of N-hexadecyl-N,N',N',N",N"-penta-n-butylguanidinium chloride via guanidinium chloride Guanidinium chloride (1.0 g, 10.5 mmol), n-butyl bromide (7.17 g, 52.4 mmol), hexadecyl bromide (3.19 g, 10.5 mmol), $K_2CO_3$, (8.67 g, 62.8 mmol) and 40 ml isobutyronitrile were refluxed for 20 hours. The solution was filtered, the acetonitrile removed and the residue refluxed in hydrochloric acid for 20 hours. The water and excess hydrochloric acid was removed to give an oil which partially crystallised on standing. NMR spectroscopy revealed a mixture of compounds.

EXAMPLE 5

One-Pot Preparation of hexa-n-butylquanidinium chloride 3 gram (31.4 mmol) guanidinium chloride, and 27.336 gram (197.8 mmol) and potassium carbonate and 27.104 g (197.8 mmol) butyl bromide were refluxed for 16 hours in isobutyronitrile (30 ml). Volatiles were removed and the residue refluxed for 1 hour with excess 6M hydrochloric acid. Volatiles were removed to leave a pasty white solid which was pure hexa-n-butylguanidinium chloride by NMR.

EXAMPLE 6

Tetrahydrofuran Hydrate Crystal Growth Tests

Tetrahydrofuran (THF) forms Structure II hydrate crystals at about 4.4° C. under atmospheric pressure. NaCl (26.28 g) and THF (99.9%, 170 g) are mixed and distilled water is added to give a final volume of 900 mL. This gives a stoichiometrically correct molar composition for making Structure II THF hydrate, $THF.17H_2O$. With this added salt the equilibrium temperature for THF hydrate formation is approximately 3.3° C. The test procedure is as follows (M. A. Kelland and L. Del Villano, Chem. Eng. Sci., 2009, 64, 3197):
1. 80 mL of the aqueous THF/NaCl solution is placed in a 100 mL glass beaker.
2. The test chemical is dissolved in this solution to give the desired concentration, for example 0.32 g of polymer in 80 ml of solution gives a 0.4 wt. % (4000 ppm) solution of the polymer.
3. The beaker is placed in a stirred cooling bath pre-set to a set temperature, e.g. −0.5° C. (±0.05° C.) which represents about 3.8° C. subcooling.
4. The solution is briefly stirred manually with a glass rod every 5 minutes, without touching the glass beaker walls, whilst being cooled for 20 minutes.
5. A hollow glass tube with inner diameter 3 mm was filled at the end with ice crystals kept at −10° C. The ice crystals are used to initiate THF hydrate formation.
6. The glass tube was placed almost halfway down in the cooled polymer/THF/NaCl solution after the solution had been cooled for 20 minutes.
7. THF hydrate crystals were allowed to grow at the end of the glass tube for 60 minutes.
8. After this time, the glass tube was removed and the amount of THF hydrate crystal formed at the tip was weighed.

Table 1 lists the results from the THF hydrate crystal growth tests.

TABLE 1

THF hydrate crystal growth in gram/hr after 1 hr growth.

| | | Concentration | | |
|---|---|---|---|---|
| Expt. | Chemical (synthetic method) | 4000 ppm | 2000 ppm | 1000 ppm |
| 1 | No additive | 1.75 | | |
| 2 | Tetra-n-butylammonium bromide | 0.23 | 0.68 | 1.19 |
| 3 | Tetra-n-pentylammonium bromide | 0.05 | 0.15 | 0.42 |
| 4 | Guanidine•HCl | 1.38 | | |
| 5 | Hexaethylguanidinium bromide (via $POCl_3$) | 0.79 | | |
| 6 | Hexa-n-propylguanidinium bromide (via $POCl_3$) | 0.65 | | |
| 7 | Hexa-n-butylguanidinium bromide (via $POCl_3$, Example 1) | 0.04 | 0.37 | 0.79 |
| 8 | Hexa-n-butylguanidinium chloride (via Guanidine•HCl, Example 2) | 0.03 | 0.18 | |
| 9 | Hexa-n-pentylguanidinium chloride (via Guanidine•HCl) | 0.81 g | | |

Experiments 5-9 show that compounds of the invention are comparable to, or an improvement, on ammonium salts. Particularly, guanidinium salts with butyl or pentyl groups are good at inhibiting the growth of THF hydrates.

EXAMPLE 7

High Pressure Gas Hydrate Kinetic Hydrate Inhibitor Tests

To evaluate the performance of the hydrate inhibitors of this invention, the examples given herein use high pressure 40 ml stainless steel rocking cells placed in a cooling bath (RC5 equipment designed by PSL Systemtechnik, Germany) and a stainless steel jacketed 23 ml stirred cell, previously described (L. Del Villano and M. A. Kelland, Chem. Eng. Sci., 2010, 65, 5366). All tests were performed using distilled water and synthetic natural gas (SNG) forming a Structure II hydrate (Table 2).

TABLE 2

Composition of synthetic natural gas (SNG).

| Component | mole % |
|---|---|
| Methane | 80.67 |
| Ethane | 10.20 |
| Propane | 4.90 |
| Iso-butane | 1.53 |
| n-butane | 0.76 |
| $N_2$ | 0.10 |
| $CO_2$ | 1.84 |

Rocking Cell Experiments

A description of the general test procedure in the rocking cells is given here:
1) The additive to be tested was dissolved or dispersed in distilled water to a specified active concentration.
2) The rocking cells were filled with 20 ml of the aqueous solution containing the additive to be tested. A steel ball was placed in each of the 5 cells and the cells sealed and placed in a cooling bath.
3) The temperature of the cooling bath was adjusted to 19.5° C., just outside the hydrate region at the pressure conditions to be used in the experiment.
4) The cell was purged twice with the SNG with stirring at 30 bar.
5) The data logging was started, and the cell was loaded with the SNG to 76 bar pressure while stirring at 600 rpm.
6) When the temperature and pressure in the cell had stabilised the cell was cooled from 19.5° C. and 76 bar to 1° C. over 18.5 hours at 600 rpm stirring.

The onset temperature (To) for hydrate formation was recorded as the first drop in pressure not due to the temperature drop in a closed system. The temperature at which fast hydrate formation occurred, Ta, was also recorded. The results are given in Table 3.

TABLE 3

Constant cooling KHI tests in 5-cell rocker rig.

| Expt | Chemical | Concentration (ppm) | Average To (° C.) | Average Ta (° C.) |
|---|---|---|---|---|
| 10 | No additive | | 18.0 | 18.0 |
| 11 | Tetra-n-butylammonium bromide | 5000 | 17.8 | 17.1 |
| 12 | Guanidine•HCl | 5000 | 17.7 | 17.6 |
| 13 | Hexa-n-butylguanidinium bromide | 5000 | 16.5 | 15.1 |
| 14 | PVCap in MEG | 2500 | 8.7 | 8.1 |
| 15 | PVCap in MEG | 5000 | 6.6 | 6.4 |
| 16 | PVCap + TBAB | 2500 + 2500 | 6.5 | 6.3 |
| 17 | PVCap + Hexa-n-butylguanidinium bromide | 2500 + 2500 | 2.2 | <2.0 |
| 17a | PVCap + Hexapropylguanidinium bromide | 2500 + 2500 | 7.3 | 4.0 |

Stirred Cell Experiments

A description of the general test procedure in the 23 ml stirred steel cell is given here:
1) The additive to be tested was dissolved or dispersed in distilled water to a specified active concentration.
2) The cell was filled with 8 ml of the aqueous solution containing the additive to be tested.
3) 8 ml of the aqueous solution containing dissolved inhibitor was placed in the cell (above the cell bottom) as well as the cell housing a pipette, and the top end piece was fitted.
4) The temperature of the cooling bath was adjusted to 19.5° C., just outside the hydrate region at the pressure conditions to be used in the experiment.
5) The cell was purged twice with the SNG with stirring at 30 bar.
6) The data logging was started, and the cell was loaded with the SNG to 76 bar pressure while stirring at 600 rpm.
7) When the temperature and pressure in the cell had stabilised the cell was cooled from 19.5° C. and 76 bar to 1° C. over 18.5 hours at 600 rpm stirring.

The onset temperature (To) for hydrate formation was recorded as the first drop in pressure not due to the temperature drop in a closed system. The temperature at which fast hydrate formation occurred, Ta, was also recorded. The results are given in Table 4.

TABLE 4

Constant cooling KHI tests in 23 ml steel cell.

| Experiment | Chemical | Concentration (ppm) | To (° C.) | Ta (° C.) |
|---|---|---|---|---|
| 18 | No additive | | 11.5 | 10.9 |
| 19 | Tetra-n-butylammonium bromide | 5000 | 11.5 | 11.2 |
| 20 | Guanidine•HCl | 5000 | 11.9 | 11.2 |
| 21 | Hexa-n-butylguanidinium bromide | 5000 | 10.7 | 8.9 |
| 22 | PVCap in MEG | 2500 | 7.9 | 6.6 |
| 23 | PVCap in MEG | 5000 | 4.8 | 4.4 |
| 24 | PVCap + TBAB | 2500 + 2500 | 6.2 | 2.5 |
| 25 | PVCap + guanidinium chloride | 2500 + 2500 | 7.8 | 6.4 |
| 26 | PVCap + Hexa-n-butylguanidinium bromide | | <1° C. | <1° C. |

Experiment 21 shows that using hexa-n-butylguanidinium bromide results in hydrate formation at a significantly lower temperature than with no additive. Experiment 26 shows that hexa-n-butylguanidinium bromide is an excellent synergistic for polyvinylcaprolactam (PVCap), better than tetrabutylammonium bromide (TBAB).

EXAMPLE 8

Anti-Agglomerant Tests

A description of the general test procedure is given here:
1. The additive to be tested was dissolved or dispersed in either 1.5 wt % aqueous NaCl solution or European white spirit to a specified active concentration based on the aqueous phase.
2. The magnet housing of the cell was filled with the aqueous solution. The magnet housing was then mounted in the bottom end piece of the cell, which thereafter was attached to the sapphire tube and the cell holder.
3. 2.5 ml of the aqueous solution, which may contain dissolved or dispersed additive, was added to the cell (above the cell bottom) using a pipette. Then 5 ml of white spirit was added. The top end piece was mounted, and the cell was placed into the cooling bath (plastic cylinder).
4. The temperature of the cooling bath was adjusted to 19.5° C., just outside the hydrate region at the pressure conditions to be used in the experiment.
5. Prior to loading the cell with recombined SNG it was purged twice by pressurising the cell to 30 bar with the SNG.

The data acquisition and video recording were started, and the cell was loaded with the SNG to the 76 bar pressure while stirring at 200 rpm. When the temperature and pressure in the cell had stabilised the stirring was stopped. The equipment was thus ready for testing the additives.

The results of all experiments were recorded by plotting temperature, pressure and torque as a function of time. The water cut was in the range 33%. The experiments were not conducted at isobaric conditions. Thus, the subcooling decreases slightly due to the loss in pressure during hydrate formation. The results are given in Table 5.

TABLE 5

Anti-agglomerant test results.

| Chemical | Concentration (ppm) | Onset Temperature (° C.) | AA Ranking | Visual Observations |
|---|---|---|---|---|
| No additive | | 11.5 | E | Plug |
| Example 3 | 10000 | 6.0 | B | Coarse dispersion of particles |
| Example 4 | 10000 | 4.0 | B | Coarse dispersion of particles |
| Example 4 | 30000 | <1° C. for 24 hrs | — | No hydrate |

The experiments described herein, were conducted at constant temperature of ca. 4° C. Thus, once the temperature and pressure had stabilised after loading the cell, the stirring was stopped. The closed cell was then cooled down to the experimental temperature, resulting in a decrease in pressure to a value Po. When the temperature and pressure had again stabilised, stirring at 700 rpm (or 100 rpm) was started.

The grading codes A-E are used to evaluate the overall performance of a chemical. Code A is best, giving loose, fine hydrates easily dispersed and no deposits in the cell. Code B gives no deposits or plug but a coarser grained dispersion of particles. Codes A and B are considered a pass.

Examples 3 and 4 at 10000 ppm give coarse grained dispersions. Example 4 at 30000 ppm resulted in no hydrate formation.

The invention claimed is:

1. A method of inhibiting the formation or agglomeration of gas hydrates in a system, said method comprising adding to the system a compound containing one or more units of formula (Ia)

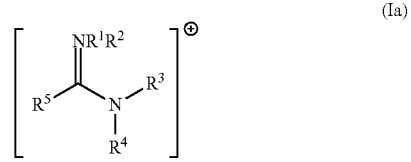

said compound optionally further comprising one or more units of formula (I)

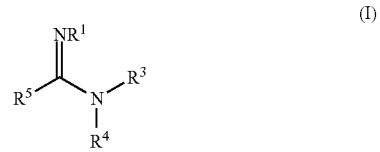

wherein:
R$^1$, R$^2$, R$^3$ and R$^4$ are independently an organic group comprising 1-20 carbon atoms and optionally one or more heteroatoms, R$^5$ is either an organic group comprising 1-20 carbon atoms and optionally one or more heteroatoms or R$^5$ is NR$^6$R$^7$ where R$^6$ and R$^7$ are an organic group comprising 1-20 carbon atoms and optionally one or more heteroatoms,
wherein R$^1$-R$^7$ may optionally act as a linker either to an adjacent unit of formula (I) or (Ia) or to a polymer chain, and
wherein at least two of R$^1$-R$^7$ denote C$_{2-6}$ alkyl.

2. The method as claimed in claim 1, wherein R$^5$ is NR$^6$R$^7$.

3. The method as claimed in claim 1, wherein
R$^1$-R$^4$, R$^6$ and R$^7$ denote C$_2$-C$_6$ alkyl;
R$^5$ denotes NR$^6$R$^7$ or C$_{2-6}$ alkyl; such that
at least two of R$^1$-R$^7$ denote C$_{3-5}$ alkyl,
wherein R$^1$-R$^7$ may optionally act as a linker either to an adjacent unit of formula (I) or (Ia) or to a polymer chain.

4. The method as claimed in claim 1, wherein when acting as
a linker to an adjacent unit of formula (I) or (Ia), R$^1$-R$^7$ denotes C$_{2-6}$ alkylene.

5. The method as claimed in claim 1, wherein
R$^1$-R$^4$, R$^6$ and R$^7$ denote C$_{3-5}$ alkyl;
R$^5$ denotes NR$^6$R$^7$ or C$_{3-5}$ alkyl;
wherein R$^1$-R$^7$ may optionally denote C$_{3-5}$ alkylene which acts as a linker either to an adjacent unit of formula (I) or (Ia) or to a polymer chain.

6. The method as claimed in claim 1 in which one or more of R$^1$-R$^7$ are independently chosen from n-butyl, n-pentyl and iso-pentyl groups.

7. The method as claimed in claim 1, wherein the compound is an oligomer or a polymer.

8. The method as claimed in claim 7, wherein the unit of formula (I) or (Ia) is a pendant group of a poly(meth)acrylate, poly(meth)acrylamide or a polymer or copolymer of N-vinylcaprolactam.

9. The method as claimed in claim 1, wherein said system is configured for hydrocarbon drilling, production, storage and/or transportation, including production, drilling, completion, fracturing, stimulation and injection and re-injection operations.

10. The method as claimed in claim 1, wherein said method inhibits the formation of gas hydrates and said compound is a polymer.

11. The method as claimed in claim 1, wherein said method inhibits the formation of gas hydrates and said compound comprises one or more units of Formula (II) or (IIa):

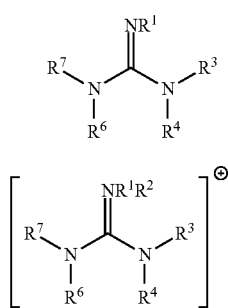

12. The method as claimed in claim 1, wherein said method inhibits the agglomeration of gas hydrates and said compound comprises one or more units of Formula (Ia) or (IIa):

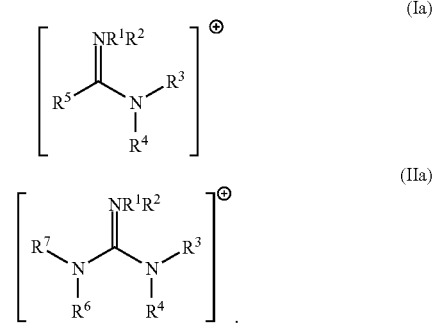

13. The method as claimed in claim 1, further comprising adding a kinetic hydrate inhibitor to said system.

14. A method of inhibiting the formation or agglomeration of gas hydrates in a system, said method comprising adding to the system a polymer containing one or more units of formula (I) or formula (Ia)

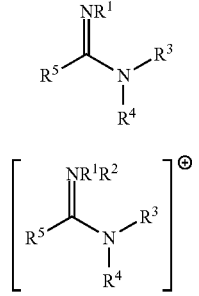

wherein
$R^1$, $R^2$, $R^3$ and $R^4$ are independently an organic group comprising 1-20 carbon atoms and optionally one or more heteroatoms, $R^5$ is either an organic group comprising 1-20 carbon atoms and optionally one or more heteroatoms or $R^5$ is $NR^6R^7$ where $R^6$ and $R^7$ are an organic group comprising 1-20 carbon atoms and optionally one or more heteroatoms, wherein $R^1$ -$R^7$ may optionally act as a linker either to an adjacent unit of formula (I) or (Ia) or to a polymer chain, and wherein at least two of $R^1$ -$R^7$ denote $C_{2-6}$ alkyl, wherein the unit of formula (I) or (Ia) is a pendant group of a poly(meth)acrylate, poly(meth)acrylamide or a polymer or copolymer of N-vinylcaprolactam.

15. The method as claimed in claim 14, wherein said compound comprises one or more units of formula (Ia).

16. The method as claimed in claim 14, wherein $R^5$ is $NR^6R^7$.

17. The method as claimed in claim 14, wherein $R^1$ -$R^4$, $R^6$ and $R^7$ denote $C_2$-$C_6$ akyl;

$R^5$ denotes $NR^6R^7$ or $C_2$-$C_6$ alkyl; such that at least two of $R^1$ -$R^7$ denote $C_{3-5}$ alkyl, wherein $R^1$ -$R^7$ may optionally act as a linker either to an adjacent unit of formula (I) or (Ia) or to a polymer chain.

18. The method as claimed in claim 14, wherein when acting as a linker to an adjacent unit of formula (I) or (Ia), $R^1$ -$R^7$ denotes $C_{2-6}$ alkylene.

19. The method as claimed in claim 14, wherein $R^1$-$R^4$, $R^6$ and $R^7$ denote $C_{3-5}$ akyl;

$R^5$ denotes $NR^6R^7$ or $C_{3-5}$ alkyl;

wherein $R^1$ -$R^7$ may optionally denote $C_{3-5}$ alkylene which acts as a linker either to an adjacent unit of formula (I) or (Ia) or to a polymer chain.

20. The method as claimed in claim 14 in which one or more of $R^1$ -$R^7$ are independently chosen from n-butyl, n-pentyl and iso-pentyl groups.

21. The method as claimed in claim 14, wherein said system is configured for hydrocarbon drilling, production, storage and/or transportation, including production, drilling, completion, fracturing, stimulation and injection and re-injection operations.

22. The method as claimed in claim 14, wherein said method inhibits the formation of gas hydrates and said compound is a polymer.

23. The method as claimed in claim 14, wherein said method inhibits the formation of gas hydrates and said compound comprises one or more units of Formula (II) or (IIa):

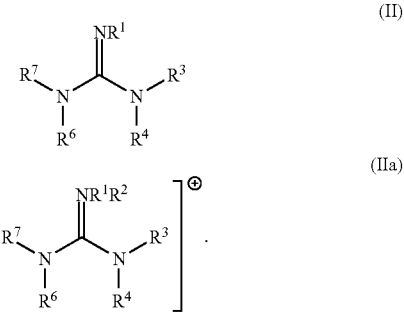

24. The method as claimed in claim 14, wherein said method inhibits the agglomeration of gas hydrates and said compound comprises one or more units of Formula (Ia) or (IIa):

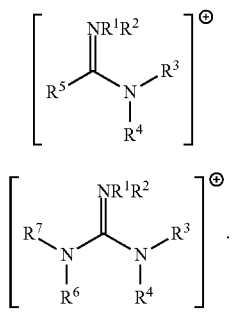

25. The method as claimed in claim 14, further comprising adding a kinetic hydrate inhibitor to said system.

26. A method of inhibiting the agglomeration of gas hydrates in a system, said method comprising adding to the system a compound containing one or more units of of Formula (Ia) or (IIa):

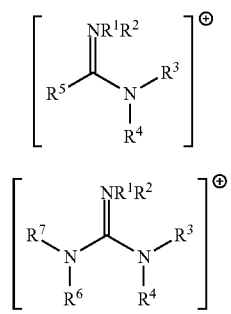

said compound optionally further comprising one or more units of formula (I)

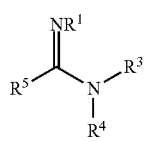

wherein
$R^1$, $R^2$, $R^3$ and $R^4$ are independently an organic group comprising 1-20 carbon atoms and optionally one or more heteroatoms, $R^5$ is either an organic group comprising 1-20 carbon atoms and optionally one or more heteroatoms or $R^5$ is $NR^6R^7$ where $R^6$ and $R^7$ are an organic group comprising 1-20 carbon atoms and optionally one or more heteroatoms,
wherein $R^1$-$R^7$ may optionally act as a linker either to an adjacent unit of formula (I) or (Ia) or to a polymer chain, and
wherein at least two of $R^1$-$R^7$ denote $C_{2-6}$ alkyl.

27. The method as claimed in claim 26, wherein said compound comprises one or more units of formula (Ia).

28. The method as claimed in claim 26, wherein $R^5$ is $NR^6R^7$.

29. The method as claimed in claim 26, wherein
$R^1$-$R^4$, $R^6$ and $R^7$ denote $C_2$-$C_6$ akyl;
$R^5$ denotes $NR^6R^7$ or $C_{2-6}$ alkyl; such that
at least two of $R^1$-$R^7$ denote $C_{3-5}$ alkyl,
wherein $R^1$-$R^7$ may optionally act as a linker either to an adjacent unit of formula (I) or (Ia) or to a polymer chain.

30. The method as claimed in claim 26, wherein when acting as a linker to an adjacent unit of formula (I) or (Ia), $R^1$-$R^7$ denotes $C_{2-6}$ alkylene.

31. The method as claimed in claim 1, wherein
$R^1$-$R^4$, $R^6$ and $R^7$ denote $C_{3-5}$ akyl;
$R^5$ denotes $NR^6R^7$ or $C_{3-5}$ alkyl;
wherein $R^1$-$R^7$ may optionally denote $C_{3-5}$ alkylene which acts as a linker either to an adjacent unit of formula (I) or (Ia) or to a polymer chain.

32. The method as claimed in claim 26 in which one or more of $R^1$-$R^7$ are independently chosen from n-butyl, n-pentyl and iso-pentyl groups.

33. The method as claimed in claim 26, wherein the compound is an oligomer or a polymer.

34. The method as claimed in claim 33, wherein the unit of formula (I) or (Ia) is a pendant group of a poly(meth)acrylate, poly(meth)acrylamide or a polymer or copolymer of N-vinylcaprolactam.

35. The method as claimed in claim 26, wherein said system is configured for hydrocarbon drilling, production, storage and/or transportation, including production, drilling, completion, fracturing, stimulation and injection and re-injection operations.

36. The method as claimed in claim 26, wherein said method inhibits the agglomeration of gas hydrates and said compound comprises one or more units of Formula (Ia) or (IIa):

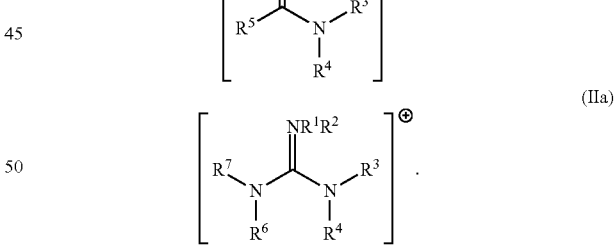

37. The method as claimed in claim 26, further comprising adding a kinetic hydrate inhibitor to said system.

* * * * *